United States Patent [19]

Bergvall

[11] Patent Number: 5,543,557

[45] Date of Patent: Aug. 6, 1996

[54] ACRYLATE MONOMER HAVING A REDUCED PRIMARY IRRITATION INDEX AND A METHOD OF MAKING SAME

[75] Inventor: Göran Bergvall, Perstorp, Sweden

[73] Assignee: Perstorp AB, Perstorp, Sweden

[21] Appl. No.: 346,385

[22] Filed: Nov. 29, 1994

Related U.S. Application Data

[63] Continuation-in-part of Ser. No. 236,690, Apr. 29, 1994, abandoned, which is a continuation of Ser. No. 958,365, Feb. 25, 1993, abandoned.

[30] Foreign Application Priority Data

Jul. 2, 1990 [SE] Sweden ................... 9002316

[51] Int. Cl.$^6$ ................... C07C 67/26
[52] U.S. Cl. ................... 560/209
[58] Field of Search ................... 560/209

[56] References Cited

U.S. PATENT DOCUMENTS

| | | |
|---|---|---|
| 3,190,927 | 6/1965 | Patton, Jr. et al. . |
| 4,118,426 | 10/1978 | Holy et al. ................... 560/209 |
| 4,767,846 | 8/1988 | Stepto et al. . |
| 4,960,952 | 10/1990 | Kemp ................... 560/209 |
| 5,010,187 | 4/1991 | Heuvelsland . |
| 5,059,719 | 10/1991 | Edwards ................... 560/209 |
| 5,118,870 | 6/1992 | Kemp ................... 560/209 |

FOREIGN PATENT DOCUMENTS

| | | |
|---|---|---|
| 0141253 | 5/1985 | European Pat. Off. . |
| 1480432 | 7/1977 | United Kingdom . |
| 2145726 | 4/1985 | United Kingdom . |

*Primary Examiner*—Paul J. Killos
*Attorney, Agent, or Firm*—Scully, Scott, Murphy & Presser

[57] ABSTRACT

A method of making an acrylate monomer from an essentially ethoxylated polyol, which monomer has a reduced and very low Primary Irritation Index (PII value). The base polyol is di, tri, tetra or polyhydroxyfunctional and the reduced PII value is obtained by reducing the formation of by-products such as monoethylene, diethylene and triethylene glycol during the ethoxylation of the base polyol. A polyol is reacted with propylene oxide at a molar ratio of 1:0.5–1:2.5 and in the presence of an alkali metal hydroxide catalyst. The polyol propoxylate obtained is reacted with ethylene oxide at a molar ratio of 1:2–1:10, whereby an ethoxylated polyol propoxylate with an average molecular weight of 270–500 is obtained. The ethoxylated polyol propoxylate is finally acrylated to yield an acrylate monomer having at least one acrylic unsaturation.

32 Claims, No Drawings

ACRYLATE MONOMER HAVING A REDUCED PRIMARY IRRITATION INDEX AND A METHOD OF MAKING SAME

This is a continuation-in-part of U.S. patent application, Ser. No. 08/236,690, filed Apr. 29, 1994, now abandoned which is a continuation of U.S. patent application, Ser. No. 07/958,365, filed Feb. 25, 1993, now abandoned.

The present invention relates to a method of making an acrylate monomer from an alkoxylated, in this case an essentially ethoxylated alcohol, which monomer has a reduced and very low Primary Irritation Index (PII value). The base alcohol, i.e. prior to alkoxylation, is di, tri, tetra or polyhydroxyfunctional (compounds hereinafter designated as polyols) and the reduced PII value is obtained by reducing the formation of by-products such as monoethylene, diethylene and triethylene glycol during the ethoxylation of the base polyol. The present invention is further directed to the acrylate monomer produced by the method of this invention.

Polyols as for instance the diols neopentyl glycol and 2-ethyl-2-butyl-1,3-propanediol, the triols trimethylolpropane and trimethylolethane, the tetrols pentaerythritol and ditrimethylolpropane, the hexols dipentaerythritol and sorbitol and the octol tripentaerythritol are essential raw materials within a number of different chemical applications. Polyols play an important role as raw materials for radiation curing acrylate esters used as monomers in various coatings, inks and adhesives. Ethoxylated polyols are to an ever increasing extent used since they combine good technical and hygienic properties, such as low toxicity and low irritation indices. There is, however, due to legislations, agreements and a continuous discussion on environmental and industrial hygienic issues, a certain and increasing demand for a further reduction of the PII values of acrylate monomers based on ethoxylated polyols.

The presence of ethylene glycols, such as monoethylene glycol, diethylene glycol and triethylene glycol, in an ethoxylated polyol will during the acrylation result in formation of corresponding acrylates. These acrylates are toxic and highly skin irritating (high PII values). This is especially valid for the diacrylate of diethylene glycol.

The irritation indices of acrylate monomers are in most cases appraised by the Draize Method (J. H. Draize et al. "Method for the Study of Irritation and Toxicity of Substances Applied Topically to the Skin and Muscous Membranes", Journal of Pharmacology and Experimental Therapeutics, 1984, 82, 377 and C.F.R. 16 Part 1000 to End, Jan. 1983, §1500.41, U.S. Federal Trade Commission). The test is performed on shaved and abraded skin of New Zealand albino rabbits. After an exposure of 24 hours, the dressings with test article extract are removed and reactions read half an hour later. Reading is also made 72 hours after application of the test article. The result is numerically expressed to the accuracy of one decimal and is the average of the irritation scores for intact and abraded skin. The scale is from 0 to 8 and the value obtained for each product is known as the Primary Irritation Index (PII).

A typical classification according to PII values is given in Table I:

TABLE I

| PII value | Classification |
| --- | --- |
| 0–0.5 | Non-irritating |
| 0.6–3.0 | Slightly irritating |
| 3.1–5.0 | Moderately irritating |
| 5.1–8.0 | Severely irritating |

Representative PII values for some acrylate monomers relevant to the present invention and enclosed embodiment examples are listed in Table II:

TABLE II

| Acrylate monomer | PII value |
| --- | --- |
| Diacrylates of ethylene glycols | ≈4–7 |
| Diacrylates of propylene glycols | ≈3–5 |
| Triacrylate of trimethylolpropane | 4.0–5.0 |
| Triacrylate of ethoxylated trimethylolpropane | 1.2–2.3 |
| Tetraacrylate of pentaerythritol | 4.5–5.5 |
| Tetraacrylate of ethoxylated pentaerythritol | 0.6–1.2 |

Methods, industrial as well as laboratory methods, normally used for ethoxylation of polyols result in formation of by-products including monoethylene glycol, diethylene glycol and triethylene glycol. These by-products are very difficult to remove since they have a low volatility, form azeotropic mixtures and have a strong affinity to the main product. It is for instance very difficult or even impossible to industrially produce an ethoxylated polyol having less than 0.4% by weight of diethylene glycol. The presence of such disturbing amounts of ethylene glycols causes increased PII values when the ethoxylated polyol is acrylated.

According to the present invention a completely new method of making an acrylic monomer based on an essentially ethoxylated polyol having very low and not disturbing amounts of monoethylene glycol, diethylene glycol and triethylene glycol has been brought about. The product can replace corresponding ethoxylated polyol without further alternations of for instance radiation curable compositions for coatings, inks, and adhesives.

The method comprises a number of steps, beginning with a reaction between a polyol and propylene oxide at a molar ratio of 1:0.5–1:2.5, preferably 1:0.6–1:1.5, using an alkali metal hydroxide catalyst, anti optionally a polar solvent, such as water. By-products propylene glycols and propyl ethers formed during the reaction are then in a second step, together with said polar solvent, evaporated. The polyol propoxylate thus obtained is in a third step reacted with ethylene oxide at a molar ratio of 1:2–1:10, resulting in an ethoxylated polyol propoxylate. The yielded product has preferably an average molecular weight of 270–500, and most preferably 300–400. The obtained ethoxylated polyol propoxylate is suitably neutralized to pH 6–8. A suitable neutralizing agent is acid sodium pyrophosphate.

The yielded ethoxylated polyol propoxylate is a clear almost colorless liquid, wherein by-products monoethylene glycol, diethylene glycol, triethylene glycol and possible ethyl ethers each amounts to less than 0.2% by weight, in most cases less than 0.1% by weight. The ash content expressed as ppm metal, is due to the low amount of catalyst, normally 0.01–0.5%, preferably 0.05–0.20 and most preferably less than 0.10%, by weight calculated as metal on base polyol, used during propoxylation and ethoxylation and the use a neutralizing agent such as acid sodium pyrophosphate, less than 2000 ppm, and in most cases less than 1500 ppm or even less than 1000 ppm being as low as 500 ppm or less.

The alkali metal hydroxide catalyst is suitably present in solid state. Potassium hydroxide is usually preferred as catalyst but other alkali metal hydroxides can be used, as well as solutions thereof. In a preferred embodiment, the alkali metal hydroxide, independent of the identity of the alkali metal, is present in a concentration of 0.05 to 0.20% by weight, calculated as metal on polyol.

A low content of ethylene glycols is essential for the possibility of obtaining acrylate monomers having very low PII values. As can be seen from Table II above, acrylates of ethylene glycols give extremely high PII values and the PII value of the ethoxylated polyol propoxylate acrylate is thus very dependent on the amount of ethylene glycols, and hence the amount of ethylene glycol acrylates. The method of the present invention gives a reduction of the Primary Irritation Index (PII), as determined by the Draize Method, from moderately irritating to slightly irritating or from slightly irritating to non-irritating. It is consequently possible to obtain acrylic monomers having a PII value of less than 1.5, preferably less than 1.0. It is, depending on used based polyol, degree of ethoxylation and degree of acrylation, also possible to obtain PII values of less than 0.5. Too high a degree of ethoxylation will result in acrylate monomers having too high a molecular weight to be used as monomers.

A low metal content (ash content) is a crucial property for the acrylation. Too high a catalyzing metal content will cause discoloration or even gelation due to acrylic polymerization.

The ethoxylated polyol propoxylate is in a fourth step acrylated through addition of acrylic unsaturation. The degree of acrylation is predetermined and yields a product having at least one acrylic unsaturation. Acrylate monomers are normally manufactured industrially either by esterification with acrylic and/or methacrylic acid or by transesterification with lower acrylate esters such as methyl, ethyl and butyl acrylate or methacrylate. The lower alcohol corresponding to the lower acrylate is during a transesterification liberated and preferably evaporated.

The base polyol is in preferred embodiments of the present invention selected from the group consisting of diols, triols, tetrols, pentols and hexols, but also monoalcohols can advantageously be used. The base polyol is in especially preferred embodiments trimethylolpropane, ditrimethylolpropane, pentaerythritol, dipentaerythritol and tripentaerythritol. Trimethylolethane and the diols neopentyl glycol and 2-ethyl-2-butyl-1, 3-propanediol are also suitable base polyols.

Yielded acrylate monomer is in preferred embodiments of the present invention a tetraacrylate of an ethoxylated pentaerythritol propoxylate, wherein the molar ratio of pentaerythritol to propylene oxide and ethylene oxide is in the range of 1:0.5:3 to 1:1.5:5 or a triacrylate of an ethoxylated trimethylolpropane propoxylate, wherein the molar ratio of trimethylolpropane to propylene oxide and ethylene oxide is in the range of 1:0.5:2 to 1:1.5:5.

The radiation curing acrylate monomer according to the present invention exhibits compared to radiation curing acrylate monomers based on ethoxylated polyols, a reduced Primary Irritation Index (PII value) without negatively influencing such important properties as viscosity, dilutability, curing rate, resistance etc. The monomer is especially suitable as monomer in ultraviolet (UV) curable compositions for coatings, inks and adhesives.

While particular embodiments of the invention will be shown in the enclosed Examples, it will be understood, of course, that the invention is not limited thereto since many modifications may be made, and it is, therefore, contemplated to cover by the appended claims any such modifications as fall within the true spirit and scope of the invention. It is, furthermore, contemplated that alkoxylation of the base polyol and acrylation of thereby obtained ethoxylated polyol propoxylate can involve preparation or manufacture in different equipments or industial plants.

As can be seen from results given in the enclosed Examples, the acrylate monomer, prepared according to the method of the present invention, does not influence other final product properties than the Primary Irritation Index. The product prepared in Example 3 is non-irritating and can be used in all kind of applications without hygienic limitations. The monomer can furthermore without recalculation or other alterations of formulations for coatings, printing inks, adhesives and the like, replace corresponding monomer based on an ethoxylated polyol.

These and other objects and the attendant advantages will be more fully understood from the enclosed embodiment examples.

Example 1: Preparation of ethoxylated pentaerythritol propoxylate.
Example 2: Preparation of ethoxylated pentaerythritol (Comparative Example).
Example 3: Preparation of a tetraacrylate from the product of Example 1.
Example 4: Preparation of a tetraacrylate from the product of Example 2 (Comparative Example).
Example 5: Comparative evaluation in UV curing lacquers containing products obtained in Examples 3 and 4.
Example 6: Determination of Primary Irritation Indices with regard to the products of Examples 3 and 4.

EXAMPLE 1

136 g (1 mole) of pentaerythritol, 0.36 g of KOH and 70 g of distilled water were charged into a 1-liter laboratory autoclave. The mixture was stirred and heated to 150° C. A nitrogen sparge was used. 58 g of propylene oxide (1 mole) was during 1 hour, at 150° C. and a pressure of 2000–4000 mm Hg, pumped into the autoclave. The temperature 150° C. was thereafter maintained during 30 minutes and followed by an evaporation of water at 150° C. and <1 mm Hg until the water content of the reaction mixture was <0.2%. Now 162.8 g of ethylene oxide (3.7 moles) were, at 150° C. and a pressure of 2500–4000 mm Hg, charged during 2 hours. A nitrogen sparge was used and the temperature 150° C. was maintained for a further 30 minutes after which time unreacted ethylene oxide was evaporated at 150° C. and <1 mm Hg.

The above obtained product was neutralized with 3% of acid sodium pyrophosphate together with 1.5% of water and 1.5% of Celite (filter aid) to pH 6–8. The mixture was stirred for 1 hour at 130° C. after which time water was evaporated at 130° C. and <1 mm Hg. The evaporation time was 30 minutes. The product was finally filtered at 100° C. and thereafter stabilized with 250 ppm of butylhydroxytoluene (BHT).

Obtained product was ethoxylated pentaerythritol propoxylate in the form of a low viscous clear liquid exhibiting the following properties:

Average molecular weight, g/mole: 356
Hydroxyl number, mg KOH/g: 629
Monoethylene glycol content, %: 0.03
Diethylene glycol content, %: 0.05
Triethylene glycol content, %: 0.06
Metal content (ash content), ppm K+Na: <100

The contents of mono, di and triethylene glycol were analyzed by means of gas chromatography and the metal content by means of flame emission spectroscopy.

EXAMPLE 2—Comparative Example 136 g (1 mole) of pentaerythritol, 0.36 g of KOH and 70 g of distilled water were charged into a 1-liter laboratory autoclave. The mixture was stirred and heated to 150° C. A nitrogen sparge was used. 57.2 g of ethylene oxide (1.3 mole) was during 1 hour, at 150° C. and a pressure of 2000–4000 mm Hg, pumped into the autoclave. The temperature 150° C. was thereafter maintained during 30 minutes and followed by an evaporation of water at 150° C. and <1 mm Hg until the water content of the reaction mixture was <0.2%. Now 162.8 g of ethylene oxide (3.7 moles) were, at 150° C. and a pressure of 2500–4000 mm Hg, charged during 2 hours. A nitrogen sparge was used and the temperature 150° C. was maintained for a further 30 minutes after which time unreacted ethylene oxide was evaporated at 150° C. and <1 mm Hg.

The above obtained product was neutralized with 3% of acid sodium pyrophosphate together with 1.5% of water and 1.5% of Celite (filter aid) to pH 6–8. The mixture was stirred for 1 hour at 130° C. after which time water was evaporated at 130° C. and <1 mm Hg. The evaporation time was 30 minutes. The product was finally filtered at 100° C. and thereafter stabilized with 250 ppm of butylhydroxytoluene (BHT).

Obtained product was ethoxylated pentaerythritol in the form of low viscous clear liquid exhibiting the following properties:
Average molecular weight, g/mole: 356
Hydroxyl number, mg KOH/g: 630
Monoethylene glycol content, %: 0.1
Diethylene glycol content, %: 0.9
Triethylene glycol content, %: 2.6
Metal content (ash content), ppm K+Na: <100
The contents of mono, di and triethylene glycol were analyzed by means of gas chromatography and the metal content by means of flame emission spectroscopy.

EXAMPLE 3

356 g (1 mole) of the product obtained in Example 1, 360 g (5 moles) of acrylic acid, 600 ml of toluene, 1000 ppm of methyl hydroquinone and 100 ppm of nitrobenzene were charged in a 4-necked reaction flask equipped with thermometer, stirrer, water-trap (Dean-Stark) and air inlet. Agitations was commenced and the reaction mixture was heated to 55°C., whereby a clear solution was obtained. 0.8% of methane sulphonic acid was now added and the mixture was heated to reflux and water separation. Air was allowed to bubble through the reaction mixture. The reflux was maintained until 98% of the theoretical esterification water was collected. Final temperature 110°C. The reaction mixture was thereafter cooled to room temperature and neutralized to pH 7 using a 5% aqueous solution of NaOH. The thus obtained salt/water phase was separated from the product/toluene phase, which was washed twice with alkaline (NaOH) water. Following the last washing and hence phase separation, remaining toluene in the product/toluene phase was vaporized at 40° C. and <10 mm Hg allowing air to bubble through.

Obtained product was tetraacrylate of ethoxylated pentaerythritol propoxylate having the following properties:
Hydroxyl number, mg KOH/g: 30
Acid number, mg KOH/g: <0.5
Viscosity, mPas: 160
Color, Gardner: 1–2

EXAMPLE 4—Comparative Example

Example 3 was repeated with the difference that 356 g (1 mole) of the product obtained in Example 2 was charged instead of the same amount of the product according to Example 1.

Obtained product was tetraacrylate of ethoxylated pentaerythritol having the following properties:
Hydroxyl number, mg KOH/g: 28
Acid number, mg KOH/g: <0.5
Viscosity, mPas: 170
Color, Gardner: 1–2

EXAMPLE 5

The acrylate monomers of Example 3 and 4 were evaluated in ultraviolet (UV) curing lacquers including a commercial acrylic polyester oligomer (Laromer LR 8799) from BASF AG of Germany and a commercial photoinitiator (Darocure 1173) from Firma E. Merck of Germany. The evaluation was directed towards the influence of the acrylate monomer of Example 3 on certain film properties in comparison to the monomer of Example 4.

The lacquer formulations contain compounds frequently used in UV curing coatings and does not necessarily give a combined Primary Irritation Index of the same dignity as the acrylate monomer prepared according to the present invention.

The lacquers were of the following formulation:

| | |
| --- | --- |
| Laromer LR 8799 | 50 g |
| Tripropylene glycol diacrylate | 25 g |
| Acrylate monomer according to Example 3 or 4 | 25 g |
| Daracure 1173 | 4 g |

Irradiation source: Labcure Unit LC9- Wallace Knight, U.K.
Belt speed: 20 m/minute.
Bulb type (UV lamp): Medium pressure quartz mercury—80 W/cm.
Number of passages under the UV lamp: 8
Coating substrate: Glass and steel panels
Coated filmthickness: ≈35 µm dry

| | Lacquer containing acrylate monomer according to | |
| --- | --- | --- |
| | Example 3 | Example 4 |
| Pendulum hardness, König secs. | 145 | 144 |
| Pencil hardness | 3H–4H | 3H–4H |
| Cupping test, mm | 6.0 | 6.0 |
| Impact resistance (Gardner), inch-lbs | 12 | 14 |

EXAMPLE 6

Products obtained according to Example 3 and 4 were evaluated with regard to their Primary Irritation Indices (PII value).

The product obtained in Example 3, tetraacrylate of ethoxylated pentaerythritol propoxylate was determined to be non-irritating having a PII value of <0.1.

The product obtained in Example 4, tetraacrylate of ethoxylated pentaerythritol was determined to be slightly irritating having a PII value of 0.6.

The test were carried out at the independent laboratories of Huntingdon Research Institute, U.K. and Scantox A/S in Denmark.

I claim:
1. A method of making an acrylate monomer comprising the steps of:
(a) reacting a polyol with propylene oxide at a molar ratio of polyol to propylene oxide of 1:0.5 to 1:2.5 and in the presence of an alkali metal hydroxide catalyst in an amount of 0.01–0.5% by weight, calculated as metal on polyol, and optionally a polar solvent, whereby yielding a polyol propoxylate and by-products propylene glycols and propyl ethers;

(b) evaporating said by-products propylene glycols and propyl ethers and said polar solvent, if present, from the product of step (a);

(c) reacting the polyol propoxylate of step (b) with ethylene oxide at a molar ratio of polyol propoxylate to ethylene oxide of 1:2 to 1:10, yielding an ethoxylated polyol propoxylate and by-products monoethylene glycol, diethylene glycol and triethylene glycol, said by-products present in an amount of less than 0.2% by weight and a metal content of less than 2000 ppm, which metal content emanates from the alkali metal hydroxide catalyst of step (a);

(d) acrylating the ethoxylated polyol propoxylate of step (c) by addition of acrylic unsaturation to yield an acrylate monomer having at least one acrylic unsaturation.

2. The method according to claim 1 wherein the molar ratio of polyol to propylene oxide in step (a) is within a range of 1:0.6 to 1:1.5.

3. The method according to claim 1 wherein the polar solvent, water is present in step (a).

4. The method according to claim 1 wherein the polyol in step (a) is selected from the group consisting of diols, triols, tetrols, pentols and hexols.

5. The method according to claim 1 wherein the polyol in step (a) is selected from the group consisting of trimethylolpropane, ditrimethylolpropane, pentaerythritol, dipentaerythritol and tripentaerythritol.

6. The method according to claim 1 wherein the amount of alkali metal hydroxide catalyst in step (a) is within a range of 0.05 to 0.20% by weight, calculated as metal on polyol.

7. The method according to claim 6 wherein the amount of alkali metal hydroxide catalyst is less than 0.10% by weight.

8. The method according to claim 1 wherein the ethoxylated polyol propoxylate of step (c) has an average molecular weight within a range of 270 to 500.

9. The method according to claim 8 wherein the average molecular weight is within a range of 300 to 400.

10. The method according to claim 1 wherein by-products monoethylene glycol, diethylene glycol and triethylene glycol in step (c), each is present in an amount of less than 0.1% by weight.

11. The method according to claim 1 wherein the ethoxylated polyol propoxylate of step (c) has a metal content of less than 1500 ppm.

12. The method according to claim 11 wherein the metal content is less than 1000 ppm.

13. The method according to claim 11 wherein the metal content is less than 500 ppm.

14. The method according to claim 1 wherein unreacted ethylene oxide and by-products monoethylene glycol, diethylene glycol and triethylene glycol and possible ethyl ethers formed in step (c) are evaporated from the ethoxylated polyol propoxylate.

15. The method according to claim 1 wherein the acrylation of step (d) is preformed by esterifing the ethoxylated polyol propoxylate of step (c) with acrylic or methacrylic acid.

16. The method according to claim 1 wherein the acrylation of step (d) is preformed by transesterification with methyl, ethyl or butyl acrylate or methacrylate, yielding the acrylate monomer of step (d) and methyl, ethyl or butyl alcohol.

17. The method according to claim 16 wherein yielded methyl, ethyl or butyl alcohol is evaporated from the acrylate monomer.

18. The method according to claim 1 wherein the acrylate monomer of step (d) is tetraacrylate of ethoxylated pentaerythritol propoxylate.

19. The method according to claim 18 wherein the ethoxylated pentaerythritol propoxylate is yielded from a molar ratio of pentaerythritol to propylene oxide and ethylene oxide being within a range of 1:0.5:3 to 1:1.5:5.

20. The method according to claim 1 wherein the acrylate monomer of step (d) is triacrylate of ethoxylated trimethylolpropane propoxylate.

21. The method according to claim 20 wherein the ethoxylated trimethylolpropane propoxylate is yielded from a molar ratio of trimethylolpropane to propylene oxide and ethylene oxide being within a range of 1:0.5:3 to 1:1.5:5.

22. The method according to claim 1 wherein the acrylate monomer of step (d) has a Primary Irritation Index (PII value) as defined and determined by the Draize Method of less than 1.5.

23. The method according to claim 22 wherein the PII value is less than 1.0.

24. The method according to claim 22 wherein the PII value is less than 0.5.

25. An acrylate monomer obtained by acrylation of an ethoxylated polyol propoxylate resulting from a process including the steps of:

(i) reacting a polyol with propylene oxide at a molar ratio of polyol to propylene oxide of 1:0.5 to 1:2.5 and in the presence of an alkali metal hydroxide catalyst and optionally a polar solvent, whereby a polyol propoxylate and by-products propylene glycols and propyl ethers are formed;

(ii) reacting the polyol propoxylate of step (i) with ethylene oxide at a molar ratio of polyol propoxylate to ethylene oxide of 1:2 to 1:10, yielding an ethoxylated polyol propoxylate having a content of by-products monoethylene glycol, diethylene glycol and triethylene glycol, each present in a concentration of less than 0.2% by weight.

26. The acrylate monomer according to claim 24 wherein said by-products propylene glycols and propyl ethers and said polar solvent is evaporated from the polyol propoxylate of step (i).

27. The acrylate monomer according to claim 25 wherein the amount of alkali metal hydroxide catalyst in step (i) is within a range of 0.05 to 0.20% by weight, calculated as metal on polyol.

28. The acrylate monomer according to claim 25 wherein the ethoxylated polyol propoxylate has a metal content of less than 1000 ppm.

29. The acrylate monomer according to claim 25, the acrylation being preformed by esterifing the ethoxylated polyol propoxylate with acrylic or methacrylic acid.

30. The acrylate monomer according to claim 25, the acrylation beings preformed by transesterification with methyl, ethyl or butyl acrylate or methacrylate.

31. The acrylate monomer according to claim 25, the acrylate monomer being tetraacrylate of ethoxylated pentaerythritol propoxylate having a Primary Irritation Index as determined by the Draize Method of less than 0.5.

32. The acrylate monomer according to claim 25, the acrylate monomer being triacrylate of ethoxylated trimethylolpropane propoxylate having a Primary Irritation Index as determined by the Draize Method of less than 1.0.

* * * * *